United States Patent
Nakano et al.

(10) Patent No.: US 11,751,898 B2
(45) Date of Patent: Sep. 12, 2023

(54) MEDICAL DEVICE AND TREATMENT METHOD

(71) Applicant: TERUMO KABUSHIKI KAISHA, Tokyo (JP)

(72) Inventors: Taiga Nakano, Cupertino, CA (US); Junichi Kobayashi, Cupertino, CA (US); Tomonori Hatta, San Jose, CA (US); Kosuke Nishio, Machida (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 114 days.

(21) Appl. No.: 17/013,913

(22) Filed: Sep. 8, 2020

(65) Prior Publication Data

US 2020/0397458 A1    Dec. 24, 2020

Related U.S. Application Data

(63) Continuation of application No. PCT/JP2019/012385, filed on Mar. 25, 2019.

(30) Foreign Application Priority Data

Mar. 28, 2018  (JP) .................................. 2018-062327

(51) Int. Cl.
   *A61B 17/22*     (2006.01)
   *A61B 17/32*     (2006.01)
   *A61B 17/3207*   (2006.01)

(52) U.S. Cl.
   CPC ........ *A61B 17/32002* (2013.01); *A61B 17/22* (2013.01); *A61B 17/320758* (2013.01);
   (Continued)

(58) Field of Classification Search
   CPC .... A61B 17/32002; A61B 2017/22078; A61B 2017/320032; A61B 2217/007; A61B 2217/005; A61B 17/32075; A61B 17/22
   (Continued)

(56) References Cited

U.S. PATENT DOCUMENTS 4,517,977 A * 5/1985 Frost ................. A61B 17/32002
                                                      604/22
6,139,214 A * 10/2000 Zirps ......................... F16D 1/10
                                                      403/328
(Continued)

FOREIGN PATENT DOCUMENTS

JP       2000508206 A    7/2000
JP       2012519023 A    8/2012
(Continued)

OTHER PUBLICATIONS

International Search Report (with English Translation) and Written Opinion issued in corresponding International Patent Application No. PCT/JP2019/012385, 9 pages (dated May 21, 2019).

(Continued)

*Primary Examiner* — Timothy J Neal
*Assistant Examiner* — Mitchell Brian Hoag
(74) *Attorney, Agent, or Firm* — BUCHANAN INGERSOLL & ROONEY PC

(57) ABSTRACT

A medical device and can remove an object inside a biological lumen while allowing a positional change of the device inside the biological lumen. The medical device includes a drive shaft, an outer tube accommodating the drive shaft, a cutting portion fixed to a distal portion of the drive shaft, and a hub unit housing proximal portions of the drive shaft and the outer tube. The hub unit has an operation unit fixed to the outer surface of the outer tube to rotate the outer tube, a first support portion rotatably supporting the (Continued)

operation unit, a first housing having an aspiration port for discharging fluid to outside, and causing communication of an aspiration lumen of the outer tube with the aspiration port, and a first seal between the first housing and the outer tube. The first support portion and the first seal are disposed in parallel along an axial direction.

18 Claims, 7 Drawing Sheets

(52) U.S. Cl.
CPC ............ *A61B 2017/22078* (2013.01); *A61B 2017/320032* (2013.01); *A61B 2217/005* (2013.01); *A61B 2217/007* (2013.01)

(58) Field of Classification Search
USPC ........................................................ 606/167
See application file for complete search history.

(56) References Cited

U.S. PATENT DOCUMENTS

| | | | |
|---|---|---|---|
| 8,475,484 B2 | 7/2013 | Wulfman et al. | |
| 2003/0083684 A1* | 5/2003 | Cesarini | A61B 17/32002 606/171 |
| 2003/0233111 A1* | 12/2003 | Patel | A61B 17/32002 606/170 |
| 2004/0230213 A1* | 11/2004 | Wulfman | A61B 5/418 606/167 |
| 2008/0004645 A1* | 1/2008 | To | A61B 17/320783 606/159 |
| 2009/0018566 A1* | 1/2009 | Escudero | A61M 25/0138 606/159 |
| 2009/0024085 A1* | 1/2009 | To | A61B 17/320758 604/95.01 |
| 2010/0152533 A1* | 6/2010 | Mark | A61B 17/32002 606/167 |
| 2011/0112563 A1* | 5/2011 | To | A61B 17/320783 604/528 |
| 2011/0118660 A1* | 5/2011 | Torrance | A61B 17/320758 604/35 |
| 2011/0301578 A1 | 12/2011 | Muniz-Medina et al. | |
| 2013/0023770 A1* | 1/2013 | Courtney | A61B 17/320758 600/478 |
| 2014/0249554 A1* | 9/2014 | To | A61B 17/320758 606/159 |
| 2015/0223788 A1* | 8/2015 | Walther | A61B 10/04 600/564 |
| 2016/0066942 A1* | 3/2016 | Nguyen | A61B 17/32002 606/171 |
| 2017/0143372 A1 | 5/2017 | Barak et al. | |
| 2017/0258488 A1 | 9/2017 | Hatta et al. | |
| 2018/0028212 A1* | 2/2018 | Akilian | A61B 17/320783 |
| 2018/0116689 A1* | 5/2018 | Nakano | A61B 17/221 |
| 2019/0117456 A1* | 4/2019 | Banko | A61M 3/0283 |
| 2019/0125363 A1* | 5/2019 | Kiersh | A61B 17/1631 |

FOREIGN PATENT DOCUMENTS

| | | |
|---|---|---|
| JP | 2014518717 A | 8/2014 |
| JP | 2017521153 A | 8/2017 |
| WO | 2016072107 A1 | 5/2016 |

OTHER PUBLICATIONS

An English Translation of the International Search Report (Form PCT/ISA/210) and the Written Opinion of the International Searching Authority (Form PCT/ISA/237) dated May 21, 2019, by the Japanese Patent Office in corresponding International Application No. PCT/JP2019/012385. (8 pages).

* cited by examiner

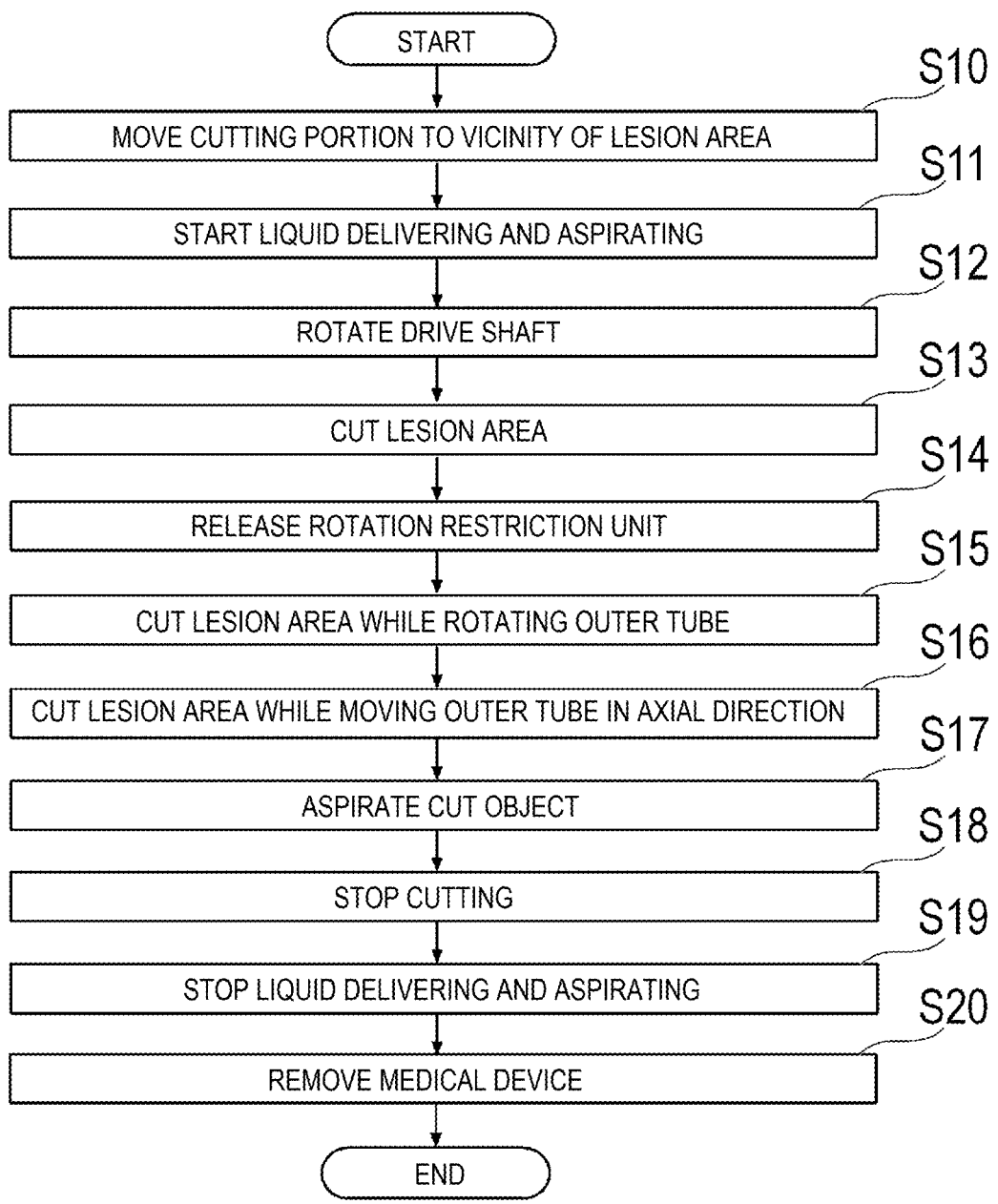

MEDICAL DEVICE AND TREATMENT METHOD

CROSS-REFERENCES TO RELATED APPLICATIONS

This application is a continuation of International Patent Application No. PCT/JP2019/012385 filed on Mar. 25, 2019, which claims priority to Japanese Patent Application No. 2018-062327 filed on Mar. 28, 2018, the entire content of both of which is incorporated herein by reference.

FIELD OF THE INVENTION

The present invention generally relates to a medical device and a treatment method for removing an object in a biological lumen.

BACKGROUND DISCUSSION

Examples of methods for treating a stenosed site caused by plaque or a thrombus in a blood vessel include widening or enlarging the blood vessel with a balloon and introducing a mesh-shaped or coil-shaped stent into the blood vessel as a support for the blood vessel. However, with these methods, it is difficult to treat the stenosed site hardened by calcification or the stenosed site appearing in a bifurcated portion of the blood vessel. As a method which enables treatment even in such a case, a method of cutting and removing a stenosed object such as the plaque and the thrombus is known.

For example, U.S. Pat. No. 8,475,484 discloses a device in which an operation head for cutting an object is fixed to a distal portion of a drive shaft. The device rotates the drive shaft, thereby enabling the operation head to cut the object. An operator's hand side of the device has a sealing structure for internally sealing the device. The sealing structure includes an injection port for injecting a sealing fluid and an aspiration port for aspirating the fluid.

SUMMARY

In a case where an orientation of the operation head of the device disclosed in U.S. Pat. No. 8,475,484 needs to be changed, it is necessary to perform an operation for changing a position of the sealing structure including the injection port and the aspiration port. However, the sealing structure is less likely to be operated since a tube is connected thereto.

The medical device and treatment method disclosed here can satisfactorily remove an object inside a biological lumen while easily changing a position of a cutting portion inside the biological lumen.

According to one aspect, the medical device for removing an object inside a biological lumen includes a rotatable drive shaft, an outer tube that accommodates the drive shaft to be rotatable, a cutting portion fixed to a distal portion of the drive shaft to cut the object, and a hub unit in which the drive shaft and a proximal portion of the outer tube are disposed. The hub unit has an operation unit fixed to an outer peripheral surface of the outer tube to rotate the outer tube, a first support portion that supports the operation unit to be rotatable, a housing having an aspiration port for discharging a fluid to an outside, and causing a lumen of the outer tube to communicate with the aspiration port, and a first seal portion disposed between the housing and the outer tube, or between the housing and the operation unit. The first support portion and the first seal portion are disposed in parallel along an axial direction.

According to another aspect, a treatment method comprises positioning a cutter in a biological lumen, wherein the cutter is connected to a distal portion of a rotatable drive shaft, with a part of the drive shaft being positioned in an outer tube, and the outer tube including a curved portion that is curved before the positioning of the cutter in the biological lumen. The method further comprises moving the cutter in the biological lumen to a vicinity of a lesion area in the biological lumen, applying an aspiration pressure to an inside of the outer tube, rotating the outer tube so that the curved portion of the outer tube changes a position of the cutter in a radial direction inside the biological lumen, rotating the drive shaft to cut the lesion area using the cutter to produce a cut object aspirating the cut object resulting from the cutting the lesion area by way of a distal portion of the outer tube; and removing the medical device from the biological lumen.

In the medical device configured as described above, the operation unit to which a force is applied during a rotary operation for changing an orientation of the outer tube is supported by the support portion. Therefore, a rotation center of the outer tube is stabilized. Furthermore, the first seal portion also supports the outer tube. Therefore, the rotation center of the outer tube is further stabilized. In this manner, when the outer tube is rotated, it is possible to prevent a decrease in adhesion of the first seal portion with respect to the outer tube or the operation unit. Therefore, it is possible to prevent air from flowing from the first seal portion into a first space portion, and an aspiration pressure in the first space portion can be properly maintained. Therefore, the medical device can satisfactorily remove the cut object while easily changing the position of the cutting portion inside the biological lumen.

According to the treatment method configured as described above, the position of the cutting portion can be effectively changed by rotating the bent outer tube of the medical device. Therefore, a lesion area can be cut and removed in a wide range inside the biological lumen.

In accordance with another aspect, a medical device for removing an object inside a biological lumen comprises a rotatable drive shaft possessing an outer surface, an outer tube and a cutter. The outer tube is a rotatable outer tube that includes a lumen in which is rotatably positioned the rotatable drive shaft so that the drive shaft can rotate relative to the outer tube, with the lumen in the outer tube including an open distal end, and the outer tube possessing an outer surface, the outer tube including a curved portion. The outer tube includes an inner surface facing the lumen, wherein the inner surface of the outer tube is spaced from the outer surface of the drive shaft so that a space exists between the inner surface of the outer tube and the outer surface of the drive shaft. The cutter is fixed to a distal portion of the drive shaft so that the cutter rotates together with the drive shaft, with the cutter being configured to be positioned in the biological lumen to cut the object inside the biological lumen when the drive shaft is rotated. A rotatable annular piece is fixed to the outer peripheral surface of the outer tube so that the annular piece and the outer tube rotate together and rotation of the annular piece results in rotation of the outer tube. The annular piece is manually operable to rotate the outer tube, and the rotation of the outer tube with the curved portion causing a position of the cutter to change in a radial direction. A housing includes an aspiration port connectable to an aspiration source for discharging a fluid to outside the medical device, with the space between the inner surface of the outer tube and the outer surface of the drive shaft being in communication with the aspiration port so that when the aspiration port is connected to the aspiration source, fluid and the object inside the biological lumen that is cut by the cutter enter the open distal end of the lumen in the outer tube, move along the space between the inner surface of the outer tube and the outer surface of the drive shaft, and are discharged to outside the medical device.

BRIEF DESCRIPTION OF THE DRAWINGS

FIG. 4 is a flowchart for describing a treatment method of the medical device.

FIG. 5A illustrates a state where cutting starts. FIG. 5B illustrates a state where cutting is performed while an outer tube is rotated. FIG. 5C illustrates a state where cutting is performed while the outer tube is moved.

FIG. 7A illustrates a state before an operation unit is rotated.

FIG. 7B illustrates a state where the operation unit is rotationally operated.

DETAILED DESCRIPTION

Figure 1:
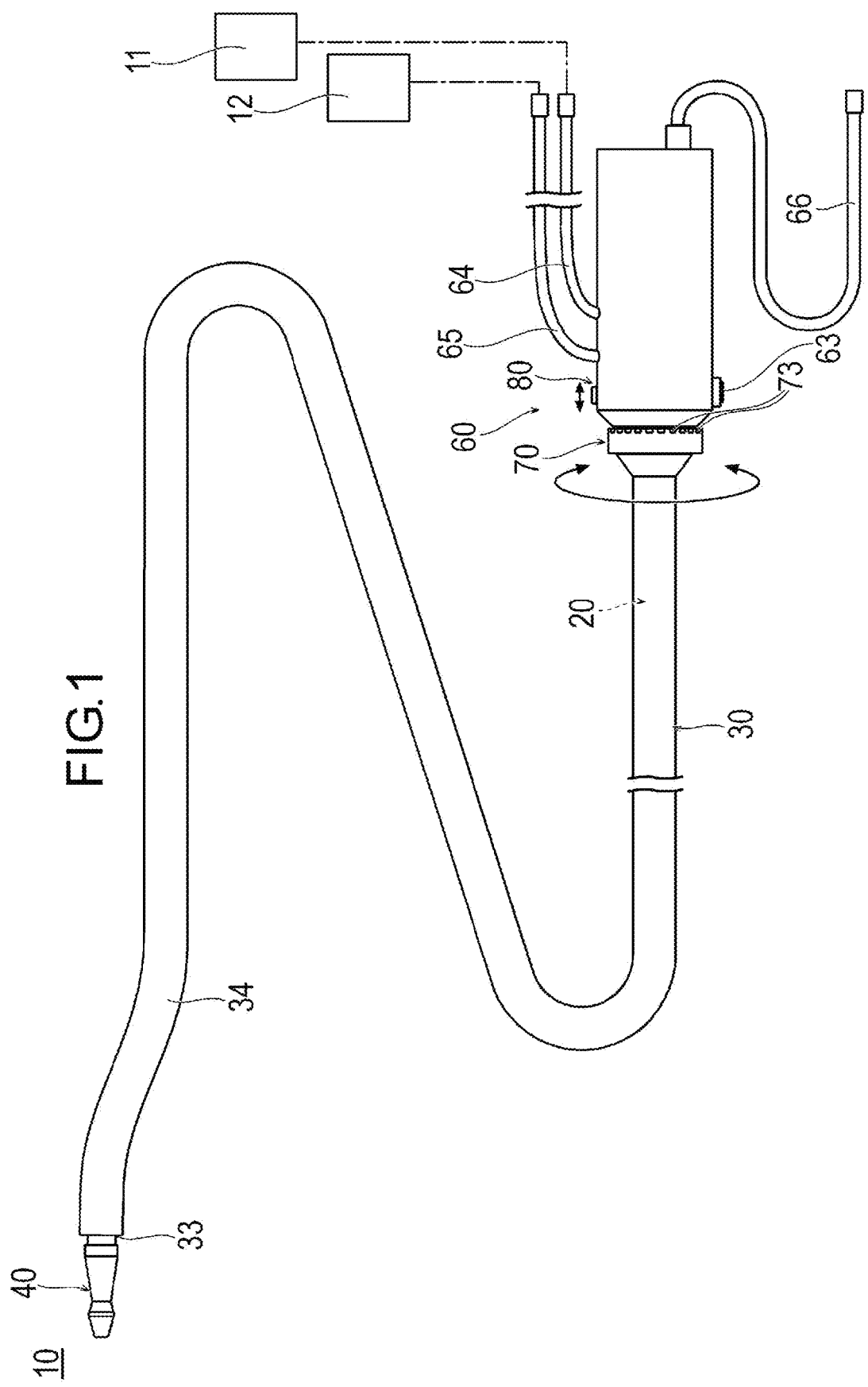
FIG. 1 is a plan view illustrating a medical device according to a first embodiment.

Set forth below with reference to the accompanying drawings is a detailed description of embodiments of a medical device and a treatment method for removing an object in a biological lumen representing examples of the inventive stent and manufacturing method disclosed here. In some cases, the size, dimension and/or ratio of features in the drawings may be exaggerated or different from actuality/reality for convenience of description and illustration.

First Embodiment

A medical device 10 according to a first embodiment may be inserted into a blood vessel in an acute lower limb ischemia or a deep vein thrombosis, and is used for a treatment to destroy (e.g., cut-up) and remove a thrombus, plaque, an atheroma, a calcified lesion, or the like. In the present specification, a side or end of the device which is inserted into the blood vessel will be referred to as a "distal side" or "distal end", and an operator's hand side will be referred to as a "proximal side" or "proximal end". The medical device and method disclosed here are not necessarily limited to removing a thrombus, plaque, an atheroma, or a calcified lesion, and the medical device and method have useful application to remove any object that may be present inside a biological lumen.

Figure 2:
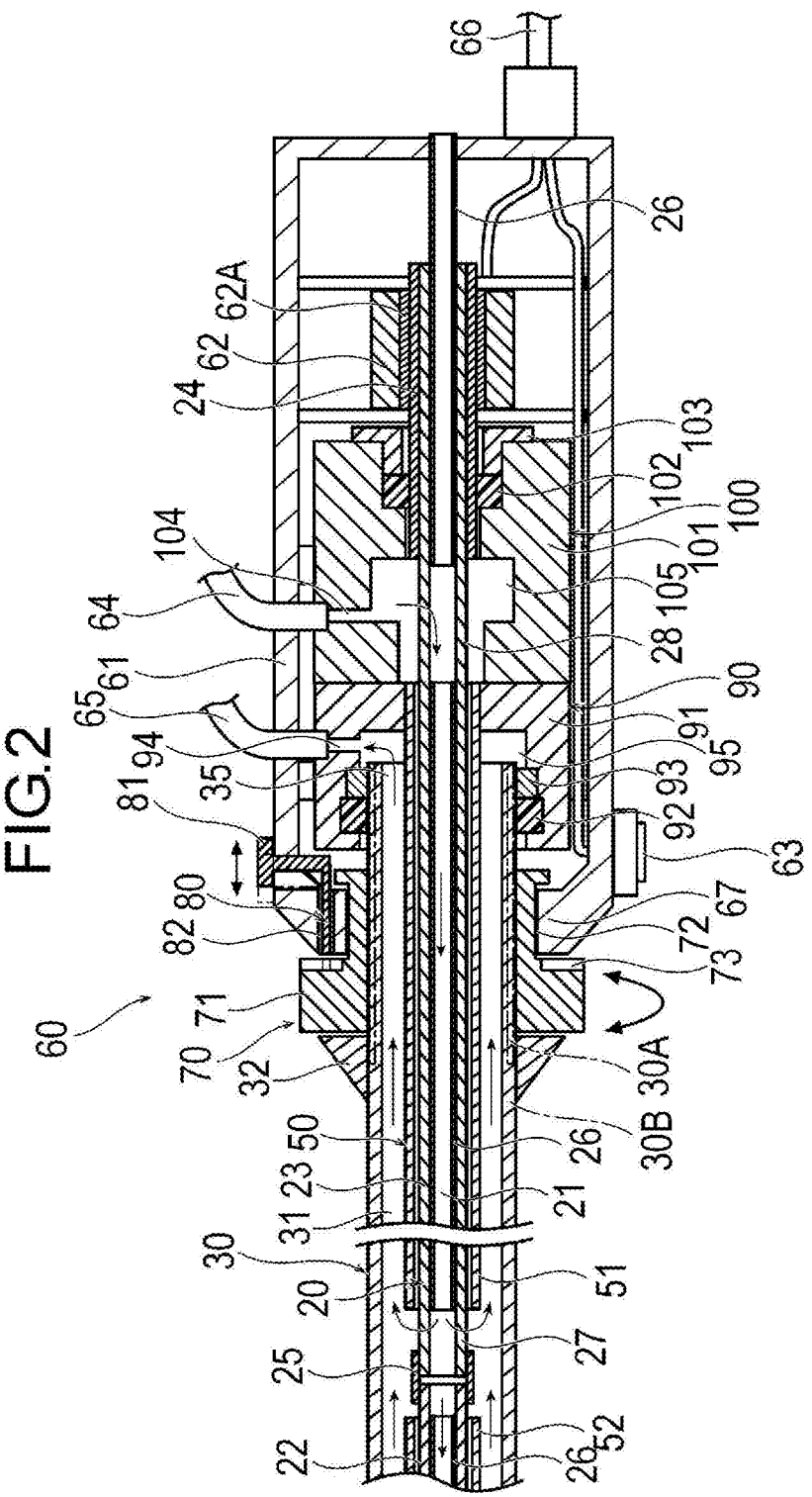
FIG. 2 is a cross-sectional view illustrating a proximal portion of the medical device.
Figure 3:
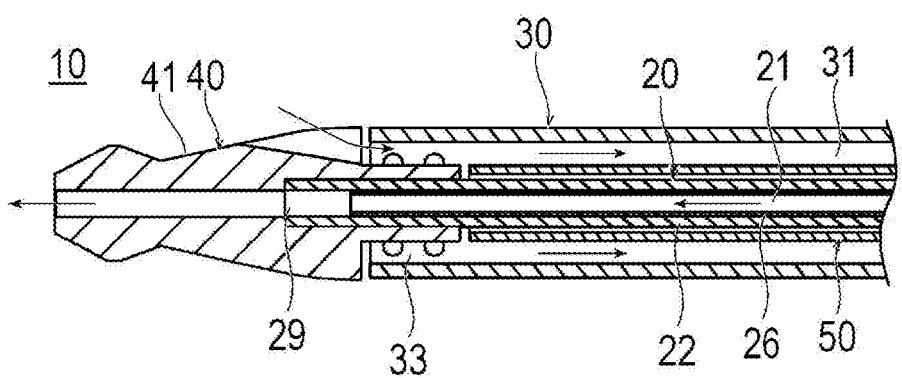
FIG. 3 is a cross-sectional view illustrating a distal portion of the medical device.

As illustrated in FIGS. 1 to 3, the medical device 10 includes an elongated drive shaft 20 that is rotationally driven, an inner tube 50 that accommodates the drive shaft, an outer tube 30 that accommodates the drive shaft 20 and the inner tube 50, a cutting portion or cutter 40 that cuts the thrombus, and a hub unit 60.

The drive shaft 20 is elongated, and transmits a rotational force to the cutting portion 40. The drive shaft 20 has a liquid delivering lumen 21 for delivering a liquid such as physiological salt solution (saline solution) to the distal side. The liquid delivering lumen 21 also serves as a guide wire lumen through which a guide wire passes. The drive shaft 20 includes a first drive shaft 22, a second drive shaft 23 located on the proximal side of the first drive shaft 22, and a connection section 24 fixed to the proximal portion of the second drive shaft 23. The drive shaft 20 further includes a tubular interlock portion 25 that interlocks the first drive shaft 22 and the second drive shaft 23 with each other, and a protective tube 26.

The first drive shaft 22 and the second drive shaft 23 are flexible, and have a characteristic in which rotational power acting from the proximal side can be transmitted to the distal side. The first drive shaft 22 and the second drive shaft 23 are tubular bodies in which a plurality of wire rods (wires) are arrayed and interlocked with each other in a spiral shape. That is, each of the drive shafts 22, 23 is formed by at least one spirally wound wire. Therefore, the first drive shaft 22 and the second drive shaft 23 allow a fluid to pass through a gap between the wire rods. Spiral winding directions of the first drive shaft 22 and the second drive shaft 23 are opposite to each other. The cutting portion 40 is fixed to a distal portion of the first drive shaft 22.

The connection section 24 is fixed to the proximal portion of the second drive shaft 23. The connection section 24 is a rigid tubular body that receives a rotational torque from a drive unit 62 (to be described later). The connection section 24 penetrates the drive unit 62, and is rotated inside the drive unit 62 via a drive rotor 62A and a bearing (not illustrated). The material from which the connection section 24 may be fabricated preferably has a certain degree of rigidity so that the torque can be effectively transmitted. For example, it is possible to preferably use a metal material such as stainless steel, Ta, Ti, Pt, Au, or W. Through laser processing, a spiral slit or groove can be formed on an outer periphery of the metal materials. In this manner, torque transmission performance can be improved. In addition, polyolefin such as polyethylene and polypropylene, polyamide, polyester such as polyethylene terephthalate, fluorine-based polymer such as polytetrafluoroethylene (PTFE) and ethylene-tetrafluoroethylene copolymer (ETFE), polyether ether ketone (PEEK), resin material such as polyimide may be used. The resin materials may be disposed on the outer periphery of the above-described metal in order to maintain rigidity.

The protective tube 26 is a tubular body that covers the insides of the first drive shaft 22, the second drive shaft 23, and the connection section 24. The protective tube 26 prevents a guide wire passing through the liquid delivering lumen 21 from rubbing against the first drive shaft 22, the second drive shaft 23, and the connection section 24. The protective tube 26 is partially disconnected in order to allow a fluid to pass therethrough inside an interlock portion between the first drive shaft 22 and the second drive shaft 23, and a second space portion 105 (to be described later). That is, as shown in FIG. 2, the protective tube 26 may be comprised of segments so that a portion of the protective tube 26 does not exist in the interlock portion between the first drive shaft 22 and the second drive shaft 23, and so that a portion of the protective tube 26 does not exist in the second space portion 105. The protective tube 26 may be continuous in the interlock portion between the first drive shaft 22 and the second drive shaft 23 so that the protective tube 26 spans across the interlock portion between the first drive shaft 22 and the second drive shaft 23. Furthermore, instead of being partially disconnected, a side hole communicating with an outer surface from an inner surface of the protective tube 26 may be provided. A proximal end of the protective tube 26 extends to a proximal end of the hub unit 60 to prevent the guide wire from rubbing inside the hub unit 60 and to guide the guide wire.

The vicinity of the interlock portion between the first drive shaft 22 and the second drive shaft 23 of the drive shaft 20 is a central passage portion 27 through which the fluid existing inside (liquid delivering lumen 21) passes outward. A portion located inside the second space portion 105 of the drive shaft 20 is a proximal passage portion 28 through which the liquid in the second space portion 105 passes inward (liquid delivering lumen 21). A distal end of the drive shaft 20 has a discharge opening portion 29 for discharging the liquid.

Examples of the material from which the first drive shaft 22 and the second drive shaft 23 may be made preferably include stainless steel, Ta, Ti, Pt, Au, W, polyolefin such as polyethylene and polypropylene, polyamide, polyester such as polyethylene terephthalate, fluorine-based polymer such as ethylene-tetrafluoroethylene copolymer (ETFE), polyether ether ketone (PEEK), or polyimide. The drive shaft 20 may not be divided into two parts, namely the first drive shaft 22 and the second drive shaft 23. The drive shaft may not be formed of a spiral wire rod (spirally wound wire). For example, the drive shaft may have a spiral slit or groove formed through, for example, laser processing.

The outer tube 30 is a cylindrical body that accommodates the drive shaft 20 and the inner tube 50. The outer tube 30 has an aspiration lumen 31 for aspirating an object such as a cut thrombus. An anti-kink protector 32 and an operation unit 70 are fixed to an outer peripheral surface of the proximal portion of the outer tube 30. The anti-kink protector 32 prevents kinks on the proximal side of the outer tube 30. In the outer tube 30, a first seal portion 92 and a second support portion 93 (to be described later) are in contact with the outer surface on the proximal side of a portion interlocked with the operation unit 70. A portion with which the operation unit 70 of the outer tube 30 is interlocked and a portion on the further proximal side are rigid. Similarly, at least some of the portion of the operation unit 70 which is interlocked with the outer tube 30 is rigid. Therefore, the outer tube 30 can be in satisfactory contact with the operation unit 70, the first seal portion (first seal) 92, and the second support portion (second seal) 93. The outer surface of the operation unit 70 which comes into contact with the first seal portion 92 and the second support portion 93 is smoothly formed to allow low friction contact. The operation unit 70 preferably has a certain degree of strength. As a material for making the operation unit 70, it is possible to preferably use ABS resin, or resin such as polycarbonate (PC), polymethyl methacrylate (PMMA), polyacetal (POM), polyphenylsulfone (PPSU), polyethylene (PE), carbon fiber, and polyether ether ketone (PEEK). A rotary operation may be stabilized by using metal such as stainless steel, Ta, Ti, Pt, Au, and W, that is, a high density material. The outer surface of the operation unit 70 which an operator touches may form a high friction surface. In this manner, a reliable and accurate rotational torque operation can be realized by the operator. The high friction surface may be formed of a biocompatible high friction material such as butyl rubber, isoprene rubber, butadiene rubber, silicone rubber, natural rubber, polyvinyl chloride (PVC), polypropylene (PP), polyethylene (PE). Alternatively, the outer surface may have irregularities so that the outer surface is easily caught by the operator's finger. The outer surface of the proximal portion of the outer tube 30 has a high frictional force except for the portion in contact with the first seal portion 92 and the second support portion 93. That is, beginning at the distal end of the outer tube 30, the frictional resistance or frictional coefficient of the outer surface of the outer tube 30 varies from a relatively lower frictional resistance or frictional coefficient (at the distal portion), to a relatively higher frictional resistance or frictional coefficient (at an intermediate portion), and to a relatively lower frictional resistance or frictional coefficient (at the proximal portion). Therefore, the outer tube 30 can be supported so that a rotational torque of the operation unit 70 is transmitted to the distal side of the medical device 10 by gripping the outer tube 30, or the outer tube 30 itself easily applies the rotational torque to the distal side of the medical device 10. Specifically, a twist or a curve is eliminated in an extracorporeally exposed portion of the outer tube 30. In this manner, the rotational torque of the operation unit 70 can be reliably transmitted to a distal end of the medical device 10.

The distal portion of the outer tube 30 is preferably more flexible than the proximal portion so that the outer tube 30 is bent inside the biological lumen. In order to have flexibility in the distal portion of the outer tube 30, for example, a spiral slit or groove may be formed through, for example, laser processing. The processed outer surface of the distal portion of the outer tube 30 may be coated with a resin.

The distal end of the outer tube 30 has an aspiration opening portion 33 for aspirating the cut object or the liquid discharged from the drive shaft 20. The distal end of the outer tube 30 is located on the proximal side of the cutting portion 40. The distal portion of the outer tube 30 has a curved portion 34. The curved portion 34 of the outer tube is permanently curved and thus exhibits the curved shape before the outer tube is positioned in a biological lumen. The curved portion 34 can be used to change a position (radial position) and an orientation of the distal end of the outer tube 30 and the cutting portion 40 by rotating the outer tube 30. The proximal end of the outer tube 30 has a proximal opening portion 35 which is open inside a first space portion 95 (to be described later).

The outer tube 30 may be configured to include a plurality of different members. For example, the outer tube 30 may be comprised of a tubular member 30B made of a resin and a reinforcing tube 30A (identified by a dashed line in FIG. 2) fixed to the outer peripheral surface of the proximal portion of the tubular member 30B. The material of the reinforcing tube 30A has higher density than the material of the tubular member 30B, and may be metal such as stainless steel, for example. The first seal portion 92 comes into contact with the outer peripheral surface of the reinforcing tube 30A.

The inner diameter of the reinforcing tube 30A is larger than the inner diameter of the tubular member 30B. Therefore, the tubular member 30B can be disposed inside and fixed to the reinforcing tube 30A. The outer diameter of the portion of the tubular member 30B where the reinforcing tube 30A is disposed may be smaller than the outer diameter of other portions of the tubular member 30B. In this manner, the outer tube 30 in which the reinforcing tube 30A is disposed in the tubular member 30B can have a constant outer diameter throughout the entity (i.e., throughout the entirety of the outer tube). Alternatively, the outer diameter of the tubular member 30B may be constant throughout the entity. In this manner, the outer diameter of the outer tube 30 in which the reinforcing tube 30A is disposed in the tubular member 30B increases in the portion where the reinforcing tube 30A is disposed. The distal end of the reinforcing tube 30A is disposed inside the anti-kink protector 32, the operation unit 70, a first support portion 67, or a casing 61 (i.e., the distal end of the reinforcing tube 30A axially overlaps the anti-kink protector 32, the operation unit 70, the first support portion 67, and a part of the casing 61). In this manner, the outer tube 30 can prevent bending in a boundary between the reinforcing tube 30A and the tubular member 30B. The outer tube 30 having the reinforcing tube 30A can effectively transmit the rotational force applied from the operation unit 70.

The material from which the outer tube 30 is preferably made has a certain degree of strength. For example, it is possible to preferably use stainless steel, Ta, Ti, Pt, Au, W, or shape memory alloy. The material from which the outer tube 30 may be fabricated may be ABS resin, or engineering plastic resin such as polycarbonate (PC), polymethyl methacrylate (PMMA), polyacetal (POM), polyphenylsulfone (PPSU), polyethylene (PE), carbon fiber, and polyetheretherketone (PEEK).

The cutting portion 40 is a member for cutting an object such as a thrombus. The cutting portion 40 is fixed to the outer peripheral surface of the distal portion of the first drive shaft 22. The outer surface of the cutting portion 40 has many fine abrasive grains. Alternatively, the cutting portion 40 may include a sharp blade.

The material from which the cutting portion 40 may be fabricated preferably has strength which enables the thrombus to be cut. For example, it is possible to preferably use stainless steel, Ta, Ti, Pt, Au, W, shape memory alloy, or super steel alloy.

The inner tube 50 is a flexible tubular body that surrounds the drive shaft 20 inside the outer tube 30. The inner tube 50 surrounds the drive shaft 20 that allows the fluid to pass between the inner surface of the drive shaft 20 and the outer surface of the drive shaft 20, thereby preventing shortcutting of the fluid from the liquid delivering lumen 21 to the aspiration lumen 31 after passing through the drive shaft 20. The inner tube 50 includes a proximal side inner tube 51 and a distal side inner tube 52. The proximal portion of the proximal side inner tube 51 is fixed to the hub unit 60. The distal portion of the proximal side inner tube 51 is located on the proximal side of the central passage portion 27 of the drive shaft 20. The proximal side inner tube 51 effectively transmits the aspiration pressure and the liquid delivering pressure of the hub unit 60 to the central passage portion 27. The distal side inner tube 52 is freely rotatable on the distal side from the interlock portion 25 without being constrained by other members. The distal side inner tube 52 effectively transmits the aspiration pressure and the liquid delivering pressure of the hub unit 60 which are transmitted to the central passage portion 27 further to the distal side. It is desirable that the material from which the inner tube 50 may be fabricated has a certain degree of flexibility and low friction. It is possible to preferably use fluorine-based polymer such as polyether ether ketone (PEEK) and PTFE/ETFE, polymethyl methacrylate (PMMA), polyethylene (PE), polyether block acid copolymer (PEBAX), or polyimide, and a combination thereof.

The hub unit 60 includes the casing 61, the drive unit 62, a switch 63, a liquid delivering port 64, an aspiration port 65, and an electric cable 66. The hub unit 60 further includes the operation unit 70, a rotation restriction unit 80, an aspiration portion 90, and a liquid delivering portion 100.

The casing 61 accommodates the drive unit 62, the liquid delivering portion 100, and the aspiration portion 90. The bearing-shaped first support portion 67 that supports the operation unit 70 to be rotatable is formed in the distal portion of the casing 61. The first support portion 67 may be separated from the casing 61.

For example, the drive unit 62 is a hollow motor. The drive unit 62 is rotated by electric power supplied from the outside via the electric cable 66. The connection section 24 of the drive shaft 20 penetrates the drive unit 62. The connection section 24 is directly connected to the hollow drive rotor 62A of the hollow motor without using a bearing or the like. Therefore, the drive unit 62 can rotate the drive shaft 20 at a high speed without deviation. The outer diameter of the connection section 24 is smaller than the outer diameter of the drive rotor 62A. Therefore, the inner diameter of a liquid delivering seal portion 102 (to be described later) is reduced when the liquid delivering seal portion 102 is brought into contact with the outer peripheral surface of the connection section 24, compared to when the liquid delivering seal portion 102 is spaced from the outer peripheral surface of the connection section 24. Therefore, the frictional resistance between the connection section 24 and the liquid delivering seal portion 102 is reduced. Accordingly, the sealing performance can be improved. A rotation speed of the drive unit 62 is not particularly limited. For example, the rotation speed is 5,000 to 200,000 rpm. In addition, another tubular body may be disposed between the hollow drive rotor 62A of the hollow motor and the drive shaft 20 in order to improve manufacturing assembly efficiency and electrical safety. The tubular body can be formed of an insulating material such as metal, non-conductive metal, or a resin. Since the hollow motor is used for the drive unit 62, the rotation axes of the drive unit 62 and the drive shaft 20 and the rotation axis of the outer tube 30 can all be coaxial with each other. In this manner, the drive shaft 20 can be very accurately and stably rotated. Moreover, it is possible to solve problems of heat generation and noise caused by drive transmission components such as gears. Furthermore, the hub unit 60 is downsized. Accordingly, an operator can operate the hub unit 60 with one hand. The connection section 24 may be a drive rotor that is a portion of the configuration of the hollow motor.

The electric cable 66 can be connected to an external power source or a control device. The switch 63 is a portion by which an operator operates the driving and stopping of the drive unit 62. The switch 63 is located on the outer surface of the distal portion of the casing 61. Therefore, the operator can operate the operation unit 70, the rotation restriction unit 80, and the switch 63 which are located in the distal portion of the casing 61 with one hand.

The operation unit 70 is operated by the operator with a finger to apply a rotational torque to the outer tube 30. The operation unit 70 is fixed to the outer peripheral surface of the proximal portion of the outer tube 30. As shown in FIG. 1, the operation unit is an annular piece. The operation unit 70 includes an operation dial 71, a receiving groove 72, and a plurality of engagement portions 73. The operation dial 71 is a substantially disk-shaped portion operated by the operator with the finger. The outer peripheral surface of the operation dial 71 has high frictional resistance or frictional coefficient so that the operation dial 71 can be easily operated. The receiving groove 72 is held to be rotatable by the first support portion 67. A contact area between the first support portion 67 and the operation unit 70 is larger than a contact area between the second support portion 93 and the outer tube 30. The plurality of engagement portions 73 are concave portions arrayed in parallel on a proximal side surface of the operation dial 71 in a circumferential direction. That is, as shown in FIG. 1, the engagement portions 73 are arranged in a common plane on a proximal part of the operation dial 71. The rotation restriction unit 80 can be fitted into the engagement portion 73. The frictional resistance or frictional coefficient of the receiving groove 72 with respect to the first support portion 67 is relatively high so that an orientation of the outer tube 30 can be held. Therefore, when the finger is released after the operation dial 71 is rotated by the operator, the rotated position is held by the frictional resistance or frictional coefficient between the receiving groove 72 and the first support portion 67. The frictional resistance or frictional coefficient between the outer peripheral surface of the outer tube 30 and the inner peripheral surface of the first seal portion 92, the frictional resistance or frictional coefficient between the outer peripheral surface of the outer tube 30 and the inner peripheral surface of the second support portion 93, or the frictional resistance or frictional coefficient between the outer peripheral surface of the operation unit 70 and the inner peripheral surface of the first support portion 67 is relatively high so that the orientation of the outer tube 30 is held. In this manner, it is possible to obtain the same advantageous effect. In this manner, the number of components can be reduced, and the structure can be simplified. Specifically, a concave and convex structure is formed on each of the outer peripheral surface and the inner peripheral surface, and the frictional resistance of the concave and convex structure is set to be high so that the orientation of the outer tube 30 can be held. Accordingly, the outer tube 30 deforms due to a force exceeding the frictional resistance.

The rotation restriction unit 80 restricts the rotation of the operation unit 70. The rotation restriction unit 80 is disposed in or at the distal portion of the casing 61 so as to be slidable with respect to the casing 61. The rotation restriction unit 80 includes a restriction operation unit 81 operated by an operator with a finger, and a projection portion (projection) 82 that is engageable with the engagement portion 73 of the operation unit 70. When the operator moves the restriction operation unit 81 to the distal side or in the distal direction, the projection portion 82 moves to the distal side or in the distal direction, and the projection portion 82 is fitted into one of the engagement portions 73 (shown in FIGS. 1 and 2). In this manner, the operation unit 70 is not rotatable. That is, the operation unit 70 is rotatably fixed. Thereafter, when the operator moves the restriction operation unit 81 to the proximal side or in the proximal direction, the projection portion 82 moves to the proximal side or in the proximal direction, and the projection portion 82 disengages from the engagement portion 73. In this manner, the operation unit 70 is rotatable. In the above description, the operation unit 70 cannot be rotated by virtue of the fitting engagement between the projection portions 82 and the engagement portions 73. However, the projection portion 82 or the engagement portion 73 may be deformable. In this alternative configuration, the operation unit 70 is rotatable only in a case where the operation dial 71 receives a prescribed or stronger rotational torque (i.e., a rotational torque causing deformation of the deformable projection portion 82/engagement portion 73 sufficient to disengage the projection portion 82 and the engagement portion 73). In addition, the prescribed or stronger rotational torque is set so that the orientation of the outer tube 30 can be held when such torque is not applied. In this manner, even in a case where the restriction operation unit 81 is not provided, the operator can change the orientation of the outer tube 30 if necessary while holding the rotated position of the outer tube 30.

The liquid delivering port 64 can be connected to a liquid delivering source 11 such as an external liquid delivering pump. A liquid such as a physiological salt solution to be delivered into the living body is supplied from the liquid delivering source 11 to the liquid delivering port 64. The liquid delivering port 64 transports the supplied liquid to the liquid delivering portion 100. The liquid delivering source 11 may have any configuration as long as the liquid delivering pressure can be generated, and it is possible to use a pump, a bag suspended in a drip tower, or a syringe, for example. The liquid delivering source 11 capable of actively delivering the liquid, such as the pump, is used. Accordingly, the liquid delivering amount can be stabilized.

The aspiration port 65 can be connected to an aspiration source 12 such as an external aspiration pump. The aspiration port 65 transports the fluid or the like aspirated by the aspiration source 12 and contained inside the aspiration portion 90, toward the aspiration source 12. The aspiration source 12 may have any configuration as long as the aspiration pressure can be generated, and it is possible to use a pump or a syringe, for example. The aspiration source 12 capable of actively aspirating the fluid, such as the pump, is used. Accordingly, the aspiration pressure can be increased, and the aspiration force can be stabilized and improved.

The aspiration portion 90 applies the aspiration pressure to the aspiration lumen 31 of the outer tube 30. The aspiration portion 90 includes a first housing 91, the first seal portion 92, and the second support portion 93.

The first housing 91 includes an aspiration port 94 that discharges the fluid to the outside, and the first space portion 95 that communicates with the aspiration port 94. The proximal opening portion 35 of the outer tube 30 is located inside the first space portion 95. The proximal side inner tube 51 is fixed to the proximal portion of the first space portion 95. The aspiration port 94 is connected to the aspiration port 65.

The first seal portion 92 is located between the first housing 91 and the outer tube 30 in the distal portion of the first space portion 95. The first seal portion 92 prevents external air from flowing into the first space portion 95. Furthermore, the first seal portion 92 supports the outer tube 30 to be rotatable. That is, the first seal portion 92 supports the outer tube 30 so that the outer tube 30 is able to rotate. The first seal portion 92 has high dimensional accuracy, a smooth surface shape, and high flexibility (elasticity). In this manner, the first seal portion 92 comes into close contact with a contact target with high dimensional accuracy without any gap, and is excellent in the sealing performance. For example, the material from which the first seal portion 92 may be fabricated includes natural rubber, synthetic rubber, and silicone resin. The first seal portion 92 may be disposed in the proximal portion of the first space portion 95. In this manner, the outer tube 30 can be very accurately supported to be rotatable, instead of increasing an entire length of the hub unit 60.

The second support portion 93 is a distal portion of the first space portion 95, and is located between the first housing 91 and the outer tube 30. The second support portion 93 is located on the proximal side of the first seal portion 92. The second support portion 93 preferably has low frictional resistance. For example, the configuration material of the second support portion 93 includes a fluorine-based resin such as ultrahigh molecular weight polyethylene, polyester, polyamide, and polytetrafluoroethylene, ABS resin, polyacetal (POM), polycarbonate (PC), or a combination of two or more materials described above (e.g., polymer alloy, polymer blend, and laminate).

The liquid delivering portion 100 is located on the proximal side of the aspiration portion 90, and is located on the distal side of the drive unit 62. The liquid delivering portion 100 delivers the liquid to the liquid delivering lumen 21 of the drive shaft 20. The liquid delivering portion 100 includes a second housing 101, the liquid delivering seal portion 102, and a fixing member 103.

The second housing 101 includes a liquid delivering port 104 through which the liquid is delivered from the outside, and the second space portion 105 that communicates with the liquid delivering port 104. The drive shaft 20 penetrates through the inside of the second space portion 105. The proximal passage portion 28 through which the liquid is delivered to the liquid delivering lumen 21 is located inside the second space portion 105. The liquid delivering port 104 is connected to the liquid delivering port 64.

The liquid delivering seal portion 102 is located between the second housing 101 and the connection section 24 of the drive shaft 20 in the proximal portion of the second space portion 105. The liquid delivering seal portion 102 prevents the liquid pressurized inside the second space portion 105 from flowing outward. The liquid delivering seal portion 102 comes into contact with the connection section 24 that rotates at high speed. Accordingly, it is preferable that the liquid delivering seal portion 102 has low frictional resistance, high heat resistance, a low linear expansion coefficient, and high wear resistance. For example, the material from which the liquid delivering seal portion 102 may be fabricated includes a fluorine-based resin such as ultrahigh molecular weight polyethylene, polyester, polyamide, and polytetrafluoroethylene, polyether ether ketone (PEEK), polyacetal (POM), silicone rubber, or a combination of two or more materials described above (e.g., polymer alloy, polymer blend, and laminate).

The fixing member 103 is a cylindrical member that fixes the liquid delivering seal portion 102 to the second housing 101. The fixing member 103 extends from the proximal side of the second housing 101 toward the inside of the second space portion 105. The distal end of the fixing member 103 is in contact with the proximal side surface of the liquid delivering seal portion 102 to support the liquid delivering seal portion 102.

Next, a method of using the medical device 10 according to the first embodiment will be described with reference to a flowchart illustrated in FIG. 4. This method of use will be described by way of example in a case of destroying (e.g., cutting or grinding) and aspirating a lesion area such as a thrombus inside the blood vessel.

Figure 5A:
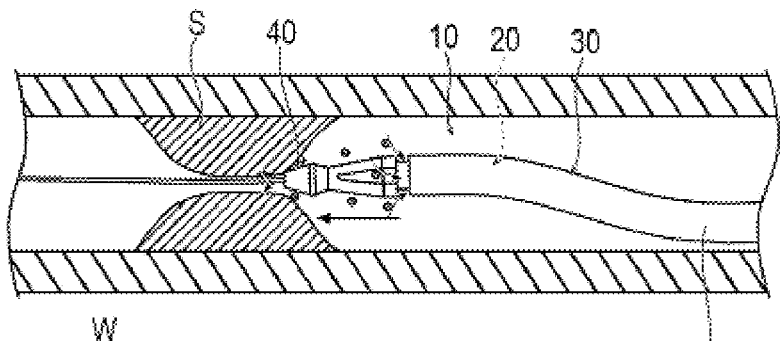
FIGS. 5A to 5C are views illustrating a state where a lesion area is removed by the medical device according to the first embodiment.

First, an operator inserts a guide wire W into the blood vessel so that the guide wire W reaches the vicinity of a lesion area S. Next, the operator inserts a proximal end of the guide wire W into the liquid delivering lumen 21 of the medical device 10. Thereafter, as illustrated in FIG. 5A, the cutting portion 40 of the medical device 10 is moved to the vicinity of the lesion area S while being guided by the guide wire W (Step S10).

Next, the operator operates the switch 63 to start liquid delivering and aspirating (Step S11). That is, the operator operates the external liquid delivering source 11 and the aspiration source 12. Simultaneously or after a lapse of a prescribed time, the cutting portion 40 is rotated via the drive shaft 20 (Step S12). The operation can be controlled by a device connected to the electric cable 66, or can be controlled by disposing a control unit inside the hub unit 60. In this manner, the operator can cut the lesion area S (Step S13).

Figure 5B:
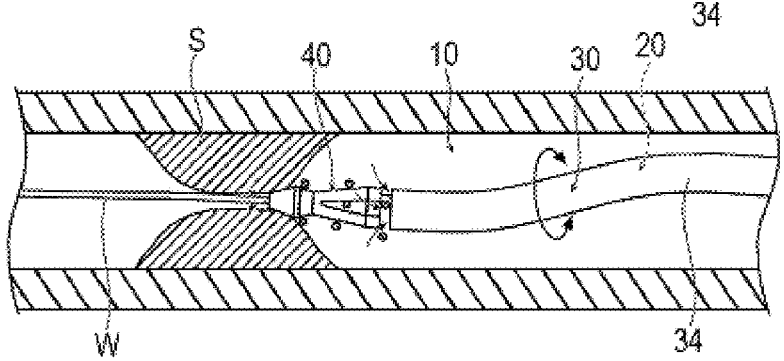
Figure 5C:
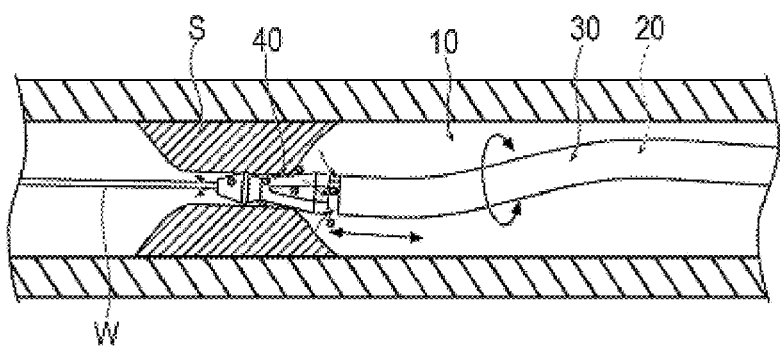

As illustrated in FIG. 2, the operator can operate the operation unit 70 in a case where the operator wants to change a position of the cutting portion 40 in a circumferential direction. Before operating the operation unit 70, the operator moves the restriction operation unit 81 of the rotation restriction unit 80 to the proximal side (Step S14). In this manner, the projection portion 82 disengages from the engagement portion 73 of the operation unit 70. Therefore, the operation unit 70 is rotatable. Next, when the operation dial 71 is rotated, the operation unit 70 supported by the first support portion 67 is rotated. In this manner, the outer tube 30 is rotated. When the outer tube 30 is rotated, the direction of the curved portion 34 of the outer tube 30 is changed. As illustrated in FIG. 5B, the position of the cutting portion 40 can be changed. Therefore, cutting (destruction) of the lesion area S can be performed while the direction of the cutting portion 40 is changed without rotating the whole hub unit 60 which is less likely to be largely rotated (Step S15). Furthermore, the operator moves the whole hub unit 60 or the extracorporeally exposed outer tube 30, and causes the outer tube 30 to reciprocate along a longitudinal direction of the blood vessel. In this manner, as illustrated in FIG. 5C, the lesion area S can be cut along the longitudinal direction of the blood vessel by the cutting portion 40 (Step S16).

When the operator operates the operation unit 70, as illustrated in FIG. 2, a force is applied to the operation unit 70 from a finger. The operation unit 70 is supported by the first support portion 67. Furthermore, the outer tube 30 to which the operation unit 70 is fixed is supported by the first seal portion 92 and the second support portion 93. Therefore, each position of the first seal portion 92 and the outer tube 30 is properly maintained. Therefore, sealing of the first seal portion 92 is properly maintained, and the air is prevented from flowing into the first space portion 95 from between the first housing 91 and the outer tube 30.

When the liquid delivering starts, the physiological salt solution (saline solution) flowing into the second space portion 105 from the liquid delivering port 104 passes through the proximal passage portion 28 of the drive shaft 20, and enters the liquid delivering lumen 21. The drive shaft 20 and the second housing 101 are sealed by the liquid delivering seal portion 102. Therefore, the physiological salt solution in the second space portion 105 is unlikely to flow out from between the drive shaft 20 and the second housing 101. Therefore, the second space portion 105 can maintain the high liquid delivering pressure.

The physiological salt solution entering the liquid delivering lumen 21 moves to the distal side. The proximal side inner tube 51 is located outside the drive shaft 20. Therefore, the physiological salt solution inside the liquid delivering lumen 21 can effectively move to the central passage portion 27 without shortcutting to the aspiration lumen 31. When a portion of the physiological salt solution inside the liquid delivering lumen 21 reaches the central passage portion 27, the physiological salt solution moves to the aspiration lumen 31.

The rest of the physiological salt solution inside the liquid delivering lumen 21 further moves to the distal side or in the distal direction, and is discharged into the blood vessel from the discharge opening portion 29 through the inside of the cutting portion 40 as illustrated in FIG. 3. A portion of the physiological salt solution entering the inside of the blood vessel is aspirated into the aspiration lumen 31 of the outer tube 30 together with the blood and the cut object(s) (Step S17). The object(s) and the fluid which enter the aspiration lumen 31 move to the proximal side or in the proximal direction through the aspiration lumen 31. As illustrated in FIG. 2, the fluid entering the aspiration lumen 31 is diluted by the physiological salt solution that merges in the central passage portion 27. Therefore, it is possible to prevent the thrombus from being formed inside the aspiration lumen 31, and it is possible to increase an aspiration amount by lowering viscosity of the aspirated object. Therefore, the aspiration performance can be improved while a decreases in the aspiration force of the medical device 10 or damage to the medical device 10 is prevented. In addition, the thrombus formed inside the medical device 10 can be prevented from flowing out into the biological lumen. When the fluid entering the aspiration lumen 31 reaches the first space portion 95 of the aspiration portion 90, the fluid is discharged from the aspiration port 94 to the external aspiration source 12. The first housing 91 of the aspiration portion 90 and the outer tube 30 are sealed by the first seal portion 92. Therefore, it is possible to prevent air from flowing between the first housing 91 and the outer tube 30. Therefore, it is possible to prevent a decrease in the aspiration pressure of the first space portion 95. The aspiration pressure at this time is 0 to 90 kPa, preferably 0 kPa to 50 kPa when absolute vacuum is set to 0 kPa.

After the cutting and aspiration of the lesion area S are completed, the operator presses the switch 63. In this manner, the rotation of the drive shaft 20 is stopped, and the cutting performed by the cutting portion 40 is stopped (Step S18). Simultaneously or after a lapse of a prescribed time, the liquid delivery and the aspiration are stopped (Step S19). That is, the external liquid delivering source 11 and the aspiration source 12 are stopped. The operation can be controlled by a device connected to the electric cable 66, or can be controlled by disposing a control unit inside the hub unit 60. Thereafter, the medical device 10 is removed from the blood vessel, and the treatment is completed (Step S20).

As described above, according to the first embodiment, there is provided the medical device 10 for removing the object inside the biological lumen. The medical device 10 includes the rotatable drive shaft 20, the outer tube 30 that rotatably accommodates the drive shaft 20, the cutting portion 40 fixed to the distal portion of the drive shaft 20 to cut the object, and the hub unit 60 in which the proximal portions of the drive shaft 20 and the outer tube 30 are disposed. The hub unit 60 has the operation unit 70 fixed to the outer peripheral surface of the outer tube 30 to rotate the outer tube 30, the first support portion 67 that rotatably supports the operation unit 70, the first housing 91 having the aspiration port 94 for discharging the fluid to the outside, and causing the aspiration lumen 31 of the outer tube 30 to communicate with the aspiration port 94, and the first seal portion 92 disposed between the first housing 91 and the outer tube 30 or between the first housing 91 and the operation unit 70. The first support portion 67 and the first seal portion 92 are disposed in parallel along the axial direction (i.e., along the axial direction of extent of the drive shaft 20).

According to the medical device 10 configured as described above, the operation unit 70 to which the force is applied from the finger during the rotary operation for changing the orientation of the outer tube 30 is supported by the first support portion 67. Therefore, the rotation center of the outer tube 30 is stabilized. Furthermore, the first seal portion 92 also supports the outer tube 30. Therefore, the rotation center of the outer tube 30 is further stabilized. In this manner, when the outer tube 30 is rotated, it is possible to prevent a decrease in adhesion of the first seal portion 92 with respect to the outer tube 30 or the operation unit 70. Therefore, it is possible to prevent the air from flowing from the first seal portion 92 into the first housing 91, and the aspiration pressure in the aspiration lumen 31 can be properly maintained. Therefore, the medical device 10 can satisfactorily aspirate the cut object(s) while changing the position of the cutting portion 40 inside the biological lumen. In addition, the first support portion 67 and the first seal portion 92 are disposed in parallel along the axial direction of the outer tube 30. In this manner, the rotation center of the outer tube 30 can be further stabilized.

In addition, the first support portion 67 is disposed on the distal side with respect to the first seal portion 92. In this manner, the first seal portion 92 can effectively support the outer tube 30 to assist the first support portion 67 on the proximal side of the first support portion 67 to which a strong force is applied from the operation unit 70. Therefore, the rotation center of the outer tube 30 is stabilized, and the sealing performance of the first seal portion 92 is unlikely to be impaired.

In addition, the hub unit 60 has the casing 61 that accommodates the first housing 91 and the second housing 101, and the first support portion 67 is a portion of the casing 61. In this manner, the rotationally operated operation unit 70 is supported by the casing 61. Therefore, the operation unit 70 is relatively easily operated. In addition, the operation unit 70 is supported by the casing 61 that accommodates the first housing 91 and the second housing 101. Therefore, the operation unit 70 easily maintains a proper position with respect to the first housing 91 and the second housing 101. Therefore, the first support portion 67 can effectively support the operation unit 70, and the rotation center of the outer tube 30 is stabilized.

In addition, the hub unit 60 has the second support portion 93 on the proximal side from the first support portion 67, and the second support portion 93 supports the outer tube 30 to be rotatable with respect to the first housing 91. In this manner, the first support portion 67 and the second support portion 93 stabilize the rotation center of the outer tube 30. Therefore, during the rotary operation of the operation unit 70, it is possible to effectively prevent a decrease in adhesion of the first seal portion 92 with respect to the outer tube 30 or the operation unit 70.

In addition, the second support portion 93 is located on the proximal side from the first seal portion 92. In this manner, the first support portion 67 and the second support portion 93 have a positional relationship of pinching the first seal portion 92 in the axial direction. Therefore, during the rotary operation of the operation unit 70, it is possible to more effectively prevent the decrease in adhesion of the first seal portion 92 with respect to the outer tube 30 or the operation unit 70.

The contact area between the first support portion 67 and the operation unit 70 is larger than the contact area between the second support portion 93 and the operation unit 70 or the outer tube 30. In this manner, the force applied from the finger to the operation unit 70 during the rotary operation can be effectively received by the first support portion 67 having the large contact area. In this manner, it is possible to effectively prevent the decrease in adhesion of the first seal portion 92 with respect to the outer tube 30 or the operation unit 70.

The medical device 10 has the rotation restriction unit 80 that restricts the rotation of the operation unit 70 with respect to the first housing 91. In this manner, the rotation of the operation unit 70 can be restricted, and the position of the outer tube 30 or the cutting portion 40 inside the living body can be fixed at any desired position.

In addition, the medical device 10 has the aspiration source 12 connected to the aspiration port 94 to actively perform aspirating. In this manner, the medical device 10 can increase the aspiration pressure, and can stabilize and improve the aspiration force.

In addition, at least a portion of the outer surface of the proximal portion of the outer tube 30 has higher friction (greater frictional coefficient) than the outer surface of the distal portion. In this manner, the operator can grip the outer tube 30, and can support the outer tube 30 so that the rotational torque of the operation unit 70 is transmitted to the distal side of the medical device 10, or can easily apply the rotational torque to the outer tube 30 itself.

In addition, the hub unit 60 has the drive unit 62 that is the hollow motor for rotating the drive shaft 20. The drive shaft 20 penetrates the drive unit 62. The rotation axis of the drive shaft 20 coincides with the rotation axis of the drive unit 62. In this manner, the rotation of the drive shaft 20 can be more accurate and stabilized. In addition, the hub unit 60 is downsized, and the operator can operate the hub unit 60 with one hand.

The disclosure here also involves a treatment method (therapeutic method). There is provided the treatment method, which may involve the medical device 10, in which the cutting portion 40 for cutting the lesion area S inside the biological lumen is disposed in the distal portion of the drive shaft 20, and in which the outer tube 30 accommodating the drive shaft 20 to be rotatable is capable of aspirating the cut lesion area S. The treatment method includes Step S10 of moving the cutting portion 40 to the vicinity of the lesion area S, Step S11 of applying aspiration pressure to the inside of the outer tube 30, Step S15 of changing the position of the cutting portion 40 inside the biological lumen by rotating the bent outer tube 30, Step S16 of causing the cutting portion 40 to cut the lesion area S by rotating the drive shaft 20, Step S17 of aspirating the cut lesion area S from the distal portion of the outer tube 30, and Step S20 of removing the medical device 10 from the biological lumen.

According to the treatment method configured as described above, the position of the cutting portion 40 can be changed by rotating the bent outer tube 30 of the medical device 10. Therefore, the lesion area S in a wide range inside the biological lumen can be effectively cut and removed.

In addition, in the cutting step, the lesion area S may be cut by the cutting portion 40 while the bent outer tube 30 inside the biological lumen is rotated. In this manner, the lesion area S can be cut while the position of the cutting portion 40 is effectively changed in the circumferential direction by rotating the bent outer tube 30. Therefore, the lesion area S in the wide range inside the biological lumen can be effectively cut and removed by the cutting portion 40.

In addition, in the cutting step, the outer tube 30 may be caused to reciprocate along the longitudinal direction of the biological lumen after the position of the cutting portion 40 is aligned in the circumferential direction by rotating the bent outer tube 30. In this manner, the lesion area S in the wide range in the longitudinal direction inside the biological lumen can be effectively cut and removed by the cutting portion 40.

In addition, in the cutting step, the fluid may be delivered to the distal side via the liquid delivering lumen 21 which is the lumen of the drive shaft 20. In this manner, the cut lesion area S can be aspirated while the fluid is supplied to the distal side by using the liquid delivering lumen 21 of the drive shaft 20. Therefore, the cut lesion area S can be effectively aspirated and removed together with the supplied fluid.

Second Embodiment

Figure 6:
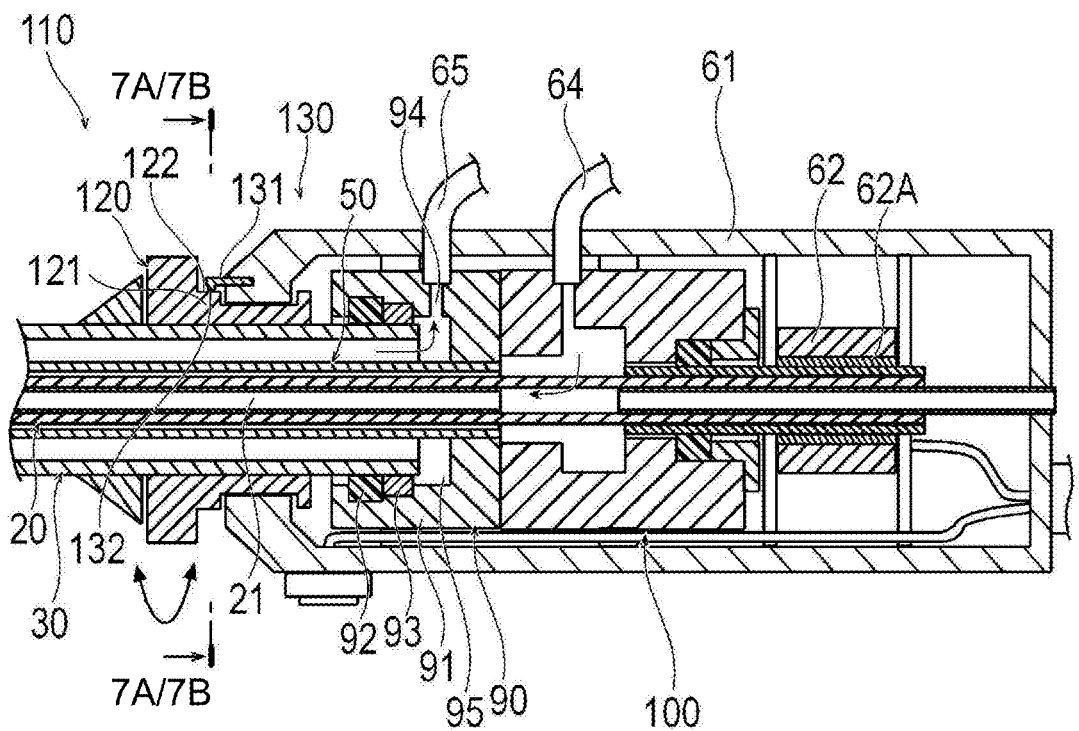
FIG. 6 is a cross-sectional view illustrating a medical device according to a second embodiment.
Figure 7A:
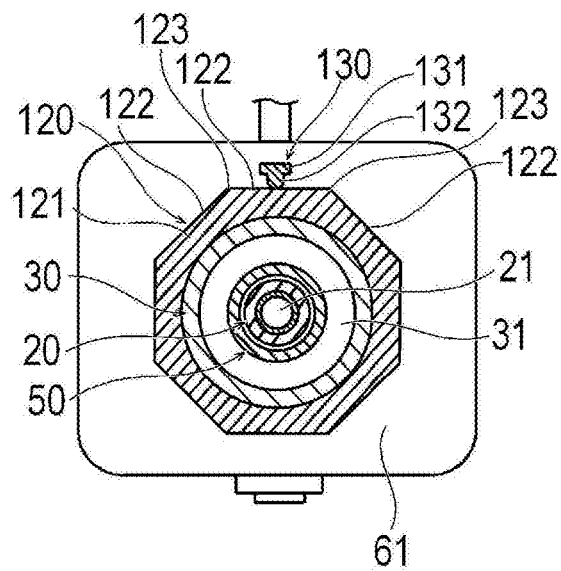
FIGS. 7A and 7B are cross-sectional views taken along the section line 7A/7B-7A/7B in FIG. 6.

As illustrated in FIGS. 6 and 7A, a medical device 110 according to a second embodiment is different from the medical device 10 according to the first embodiment in the configuration of a rotation restriction unit 130. In the description below, features that are the same or similar to those described above are identified by the same reference numerals and a detailed description of such features is not repeated.

An operation unit 120 of the medical device 110 has a polygonal portion 121 whose axially orthogonal cross section is polygonal. A plurality of surfaces formed on the outer peripheral surface of the polygonal portion 121 are engagement portions 122. In the illustrated embodiments, the engagement portions 122 are flat surface portions.

The rotation restriction unit 130 includes a leaf spring-shaped elastic portion 131 that projects from the distal portion of the casing 61 in the distal direction, and a projection portion 132 that projects from the elastic portion 131. The elastic portion 131 extends from the casing 61 to the outside of the polygonal portion 121. The projection portion 132 projects from the elastic portion 131 toward the polygonal portion 121, and is in contact with the engagement portion 122. The elastic portion 131 biases the projection portion 132 toward the engagement portion 122.

Figure 7B:
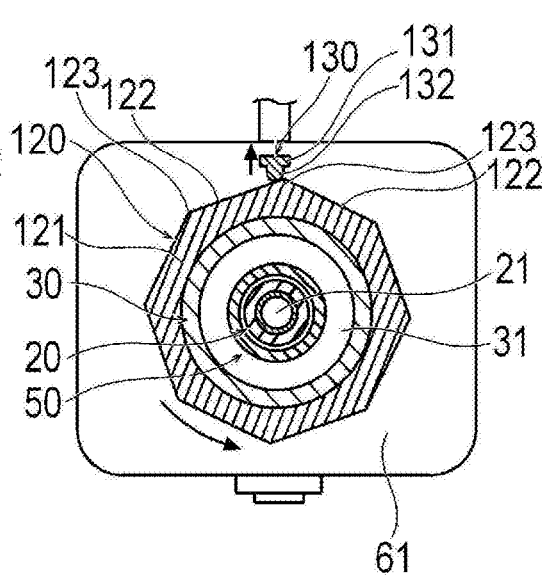

When an operator rotates the operation dial 71, a contact position between the projection portion 132 and the engagement portion 122 is changed as illustrated in FIG. 7B. The elastic portion 131 is bent most when the projection portion 132 crosses over a boundary between the two engagement portions 122, that is, a corner portion 123 of the polygonal shape. Therefore, when the projection portion 132 crosses over the corner portion 123, the rotational resistance of the operation unit 120 is maximized. Therefore, when the operator stops the rotary operation of the operation dial 71, the projection portion 132 does not cross over the subsequent corner portion 123, and the rotation is restricted. Therefore, the rotation restriction unit 130 can restrict the rotation of the operation unit 120 and the outer tube 30 with respect to the casing 61 and the first housing 91. In this manner, the position of the cutting portion 40 is properly held in a state where the operator does not operate the operation unit 120. Therefore, operability of the medical device 110 is improved.

Third Embodiment

Figure 8:
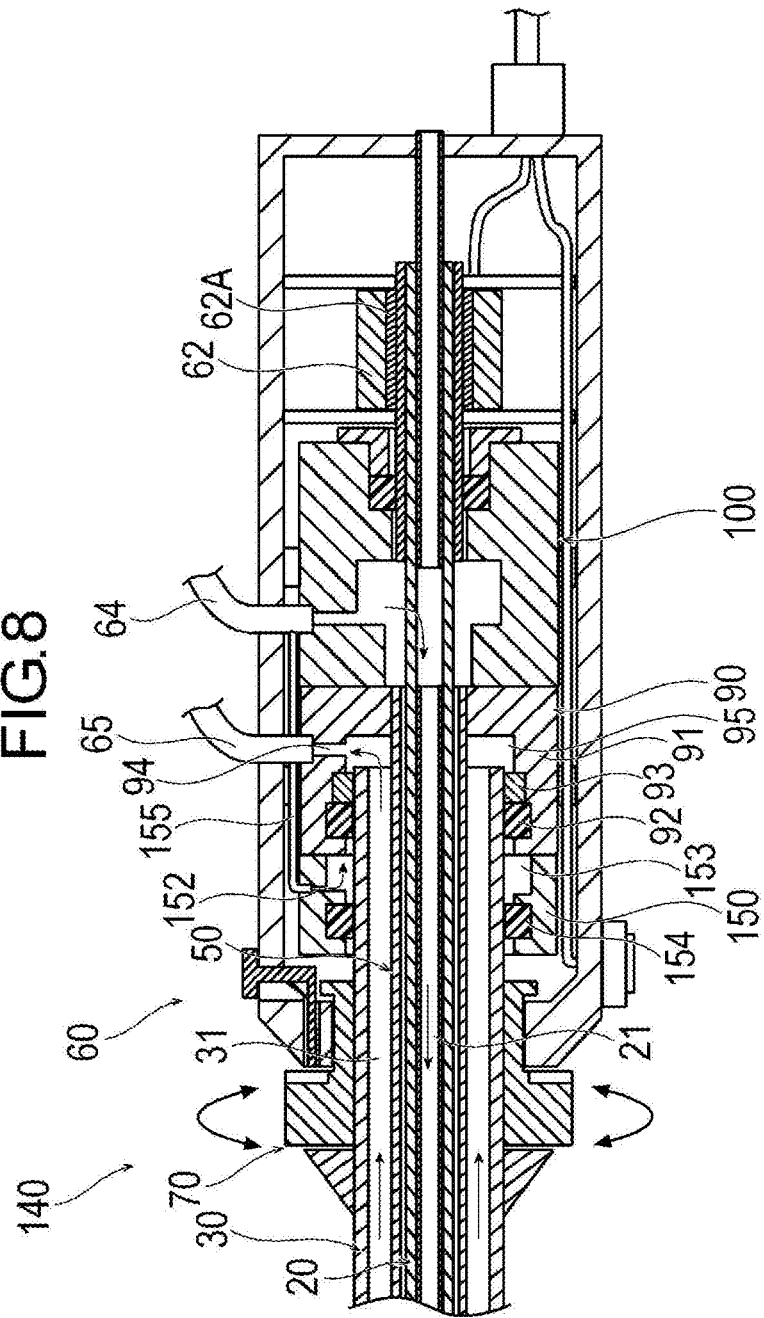
FIG. 8 is a cross-sectional view illustrating a proximal portion of a medical device according to a third embodiment.

A medical device 140 according to a third embodiment is different from the medical device 10 according to the first embodiment in that an auxiliary housing 150 is provided as illustrated in FIG. 8. In the description below, features that are the same or similar to those described above are identified by the same reference numerals and a detailed description of such features is not repeated.

The medical device 140 includes the auxiliary housing 150 on the distal side of the first housing 91 of the hub unit 60. The auxiliary housing 150 includes an auxiliary liquid delivering port 152 through which the liquid is delivered from the outside, and an auxiliary space portion 153 that communicates with the auxiliary liquid delivering port 152. The auxiliary space portion 153 is located on the distal side of the first seal portion 92 of the first housing 91. The outer tube 30, the inner tube 50, and the drive shaft 20 penetrate the inside of the auxiliary space portion 153. A second seal portion (second seal) 154 is disposed on the distal side of the auxiliary space portion 153.

The second seal portion 154 is located between the auxiliary housing 150 and the outer tube 30 in the distal portion of the auxiliary space portion 153. The second seal portion 154 prevents the liquid pressurized inside the auxiliary space portion 153 from flowing outward. Furthermore, the second seal portion 154 supports the outer tube 30. The second seal portion 154 has high dimensional accuracy, a smooth surface shape, and high flexibility (elasticity). In this manner, the second seal portion 154 comes into close contact with a contact target with high dimensional accuracy without any gap, and is excellent in the sealing performance. Examples of the material from which the second seal portion 154 may be fabricated include natural rubber, synthetic rubber, and silicone resin.

The liquid is delivered to the auxiliary liquid delivering port 152 from an auxiliary port 155 connected to the liquid delivering port 64. When the liquid amount is excessively supplied from the auxiliary port 155, the liquid flows into the auxiliary liquid delivering port 152 more than necessary via the second seal portion 154. As a result, the amount of the liquid aspirated from the distal end of the medical device 140 decreases, and thus, original aspiration performance is degraded. The auxiliary port 155 has a narrower flow path than the liquid delivering port 64. Therefore, due to a pressure loss of the auxiliary port 155, the amount of the liquid reaching the auxiliary liquid delivering port 152 is less than the amount of the liquid reaching the liquid delivering port 104 of the liquid delivering portion 100. Therefore, while the liquid is supplied to the auxiliary liquid delivering port 152, the liquid is not excessively supplied, and the treatment can be performed without impairing the liquid amount aspirated from the distal end of the medical device 140. At the same time, the second space portion 105 of the liquid delivering portion 100 can be filled with the liquid.

When the aspiration portion 90 starts aspirating, the object such as the aspirated lesion area or the liquid reaches the first space portion 95 of the aspiration portion 90 through the aspiration lumen 31. The object(s) or the liquid reaching the first space portion 95 is discharged from the aspiration port 94 to the external aspiration source 12. The first housing 91 of the aspiration portion 90 and the outer tube 30 are sealed by the first seal portion 92. Therefore, it is possible to prevent the air flowing from between the first housing 91 and the outer tube 30. The auxiliary space portion 153 is disposed on the distal side of the first seal portion 92. The auxiliary space portion 153 is filled with the liquid such as a physiological salt solution (saline solution) supplied from the auxiliary liquid delivering port 152 via the auxiliary port 155. Then, the liquid in the auxiliary space portion 153 is sealed by the first seal portion 92 and the second seal portion 154 which are in contact with the outer tube 30. Therefore, even if the sealing performance of the first seal portion 92 is degraded, the fluid entering the first space portion 95 through a gap between the first seal portion 92 and the outer tube 30 is not air, and the liquid that fills the auxiliary space portion 153. Therefore, it is possible to prevent air from flowing into the first space portion 95. Therefore, it is possible to reliably prevent a decrease in the aspiration pressure of the first space portion 95.

In the auxiliary space portion 153, the auxiliary liquid delivering port 152 may be closed in a state where the fluid is sealed. In addition, at least one of the first seal portion 92 and the second seal portion 154 may have low sealing performance so that the auxiliary space portion 153 can be relatively easily primed, and may be configured so that the liquid can be easily circulated.

The present invention is not limited to the above-described embodiments, and various modifications can be made by those skilled in the art within the technical idea of the present invention. For example, the biological lumen into which the medical device is inserted is not limited to the blood vessel, and may be a vessel, a ureter, a bile duct, a fallopian tube, or a hepatic duct, for example. Therefore, the object(s) to be destroyed is not limited to the thrombus.

In addition, the first housing 91, the second housing 101 and the auxiliary housing 150 may be integrally formed.

In addition, the aspiration port 94 of the aspiration portion 90 may be open to the atmosphere without being connected to the aspiration source 12. According to this configuration, even in a case where the pressure inside the biological lumen is higher than the atmospheric pressure, the aspiration portion 90 can aspirate the object inside the biological lumen.

The detailed description above describes embodiments of a medical device and a treatment method for removing an object in a biological lumen representing examples of the inventive medical device and treatment method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for removing an object inside a biological lumen, comprising:
   a rotatable drive shaft extending along an axial direction and rotatable about a rotation axis that extends in the axial direction;
   a rotatable outer tube in which is rotatably accommodated the drive shaft, the outer tube being rotatable relative to the drive shaft and including a lumen, the outer tube possessing an open distal end and an open proximal end;
   a cutter fixed to a distal portion of the drive shaft to cut the object, a distal portion of the cutter being positioned distally beyond the open distal end of the outer tube;
   a hub unit in which a portion of the drive shaft and a proximal portion of the outer tube are disposed,
   the hub unit comprising:
      an operation unit fixed to an outer peripheral surface of the outer tube so that the operation unit and the outer tube rotate together;
      a first support portion that rotatably supports the operation unit, the operation unit being rotatable relative to the first support portion;
      a housing having a port for discharging a fluid to outside the medical device, the lumen of the outer tube being in communication with the port by way of the open proximal end of the outer tube so that the fluid in the lumen of the outer tube flows in a proximal direction toward the open proximal end of the outer tube, exits the lumen of the outer tube at the open proximal end of the outer tube and enters the port to flow to outside the medical device;
      a first seal portion disposed between the housing and the outer tube, or between the housing and the operation unit; and the first support portion and the first seal portion being disposed parallel along the axial direction.

2. The medical device according to claim 1, wherein the first support portion is disposed entirely on a distal side of the first seal portion.

3. The medical device according to claim 1, wherein the hub unit includes a casing that accommodates the housing, and wherein the first support portion is a portion of the casing.

4. The medical device according to claim 1, wherein the hub unit includes a second support portion on a proximal side of the first support portion, the second support portion rotatably supporting the outer tube so that the outer tube is rotatable with respect to the housing.

5. The medical device according to claim 4, wherein the second support portion is located on the proximal side of the first seal portion.

6. The medical device according to claim 4, wherein the first support portion rotatably supports the operation unit by virtue of the first support portion being in contact with the operation unit in a first contact area, the second support portion being in contact with the operation unit or the outer tube in a second contact area, the first contact area being larger than the second contact area.

7. The medical device according to claim 1, wherein the housing surrounds an auxiliary space located distal of the first seal portion, the auxiliary space communicating with an auxiliary liquid delivering port to which a liquid is supplied so that the liquid supplied to the auxiliary liquid delivering port flows into the auxiliary space, and further comprising a second seal portion disposed between a distal side of the auxiliary space and the outer tube.

8. The medical device according to claim 1, further comprising: a projection and an engagement portion of the operation unit that are engageable with each other to prevent rotation of the operation unit with respect to the housing, the projection and the engagement portion of the operation unit being disengageable with each other to permit rotation of the operation unit with respect to the housing.

9. The medical device according to claim 1, wherein the operation unit is a manually rotatable dial that possesses an outer surface, the outer surface of the annular part including an annular groove in which is positioned the first support portion.

10. The medical device according to claim 1, wherein at least a portion of an outer surface of a proximal portion of the outer tube possesses a frictional coefficient higher than a frictional coefficient of an outer surface of a distal portion of the outer tube.

11. The medical device according to claim 1, wherein the hub unit includes a drive unit that is a hollow motor operatively connected to the drive shaft for rotating the drive shaft, the drive shaft passing through the drive unit, and the rotation axis of the drive shaft coincides with a rotation axis of the drive unit.

12. The medical device according to claim 1, further comprising an aspiration source connected to the port.

13. A medical device for removing an object inside a biological lumen, comprising:
a rotatable drive shaft possessing an outer surface;
a rotatable outer tube that includes a lumen in which is rotatably positioned the rotatable drive shaft so that the drive shaft can rotate relative to the outer tube, the lumen extending throughout a longitudinal extent of the outer tube, the lumen in the outer tube including an open distal end and an open proximal end, the outer tube possessing an outer surface, the outer tube including a curved portion that is curved along a portion of the longitudinal extent of the outer tube, the outer tube including an inner surface facing the lumen, the inner surface of the outer tube being spaced from the outer surface of the drive shaft so that a space exists between the inner surface of the outer tube and the outer surface of the drive shaft;
a cutter fixed to a distal portion of the drive shaft so that the cutter rotates together with the drive shaft, a distal portion of the cutter being positioned distally beyond the open distal end of the lumen in the outer tube, the cutter being configured to be positioned in the biological lumen to cut the object inside the biological lumen when the drive shaft is rotated;
a rotatable annular piece fixed to an outer peripheral surface of the outer tube so that the annular piece and the outer tube rotate together and manual rotation of the annular piece results in rotation of the outer tube, the annular piece being manually operable to rotate the outer tube, and the curved portion of the outer tube causing a position of the cutter to change in a radial direction when the outer tube is rotated; and
a housing that includes a port for discharging a fluid to outside the medical device, the space between the inner surface of the outer tube and the outer surface of the drive shaft being in communication with the port by way of the open proximal end of the lumen so that fluid and the object inside the biological lumen that is cut by the cutter enter the open distal end of the lumen in the outer tube, move along the space between the inner surface of the outer tube and the outer surface of the drive shaft, and are discharged to outside the medical device by way of the port.

14. The medical device according to claim 13, wherein the housing is positioned in a casing, the casing including a distal portion at which is located a support portion that rotatably supports a part of the annular piece.

15. The medical device according to claim 14, further comprising a seal positioned between and in contact with the housing and an outer surface of the outer tube, the seal being positioned completely proximal of the support portion.

16. The medical device according to claim 14, wherein the annular piece includes a part that is manually operated to rotate the annular piece, the part of the annular piece that is rotatably supported by the support portion being positioned proximal of the part of the annular piece that is manually operated.

17. The medical device according to claim 16, further comprising a seal positioned between and in contact with the housing and an outer surface of the outer tube, the seal being positioned completely proximal of the part of the annular piece that is rotatably supported by the support portion.

18. The medical device according to claim 13, further comprising a slidable projection that is slidable relative to the annular piece and an engagement portion on the annular piece, the projection and the engagement portion being engageable with each other to prevent rotation of the annular piece with respect to the housing, the projection and the engagement portion being disengageable with each other to permit rotation of the annular piece with respect to the housing.

* * * * *